(12) United States Patent
Alam et al.

(10) Patent No.: US 11,615,869 B1
(45) Date of Patent: Mar. 28, 2023

(54) SYSTEM AND METHOD FOR LONGITUDINAL NON-CONFORMING MEDICAL DATA RECORDS

(71) Applicant: QUINTILES IMS INCORPORATED, Danbury, CT (US)

(72) Inventors: Navdeep Alam, Wayne, PA (US); Anfisa Kaydak, Huntingdon Valley, PA (US); Kannan Nair, Chester Springs, PA (US)

(73) Assignee: IQVIA Inc., Parsippany, NJ (US)

( * ) Notice: Subject to any disclaimer, the term of this patent is extended or adjusted under 35 U.S.C. 154(b) by 535 days.

(21) Appl. No.: 15/136,772

(22) Filed: Apr. 22, 2016

(51) Int. Cl.
G16H 10/60 (2018.01)
G16H 20/10 (2018.01)
H04L 9/30 (2006.01)

(52) U.S. Cl.
CPC ............. *G16H 10/60* (2018.01); *G16H 20/10* (2018.01); *H04L 9/30* (2013.01)

(58) Field of Classification Search
CPC .. G06Q 20/10; G06Q 50/22–24; G06Q 10/60; G16H 10/60; G16H 20/10; G06F 19/3456; H04L 9/30
See application file for complete search history.

(56) References Cited

U.S. PATENT DOCUMENTS

| | | | | |
|---|---|---|---|---|
| 5,121,470 A | * | 6/1992 | Trautman | A61B 5/00 345/440 |
| 6,347,329 B1 | * | 2/2002 | Evans | G06F 19/325 709/202 |
| 6,691,101 B2 | * | 2/2004 | MacNicol | G06F 16/24556 707/714 |
| 2004/0162740 A1 | * | 8/2004 | Ericsson | G06Q 10/10 705/3 |
| 2008/0065452 A1 | * | 3/2008 | Naeymi-Rad | G06Q 50/22 705/1.1 |
| 2010/0070306 A1 | * | 3/2010 | Dvorak | G06F 19/00 705/3 |
| 2012/0029938 A1 | * | 2/2012 | Lauter | G06F 21/6254 705/2 |
| 2012/0136678 A1 | * | 5/2012 | Steinberg | G16H 80/00 705/3 |

* cited by examiner

*Primary Examiner* — Robert A Sorey
*Assistant Examiner* — Kimberly A. Sass
(74) *Attorney, Agent, or Firm* — Fish & Richardson P.C.

(57) ABSTRACT

A computer-assisted method including obtaining healthcare records from multiple different data sources that each provide information regarding a corresponding type of healthcare events, identifying healthcare records from the multiple different data sources that are for a healthcare event associated with a particular individual and that occurred during a particular period of time, and generating a composite record for the particular individual for the particular period of time, and storing the composite record in a database of composite records. The composite record include an identifier for the particular individual, a pharmaceutical transactions array, where each entry in the pharmaceutical transactions array represents a pharmaceutical transaction that occurred during the particular period of time, and a medical visit array, where each entry in the medical visit array represents a medical visit that occurred during the particular period of time.

21 Claims, 5 Drawing Sheets

SYSTEM AND METHOD FOR LONGITUDINAL NON-CONFORMING MEDICAL DATA RECORDS

BACKGROUND

Medical patients may receive various treatments. For example, a medical patient may be prescribed medication by a healthcare professional. A medical record indicating the prescription for the medical patient may be generated. Medical records may be generated by labs, hospital, medical insurance companies, or long term care facilities.

SUMMARY

Modern database systems often exhibit problems with computational efficiency due to significantly large data volumes received from distributed data sources. For instance, raw data from data sources often need to be gathered, organized, and additionally processed in order to generate aggregate data metrics that are used for predictive analytics. Analyzing disparate records from across different databases can be computationally burdensome to the extent that many desirable database operations are precluded across large and complex databases. For example, in the health care field, a variety of epidemiological studies would reveal links between disparate events. These problems are particularly acute in that the underlying databases may be de-identified in order to satisfy medical privacy concerns. Further, the size of the databases, which can include complex coding for complex and disparate diagnoses may make establishing links between different events even more computationally intensive as a specified item may be compared against countless other items, diagnoses, stimuli, and conditions. These operations are further complicated by different data sources that are formatted in different conventions and with varying degrees of completeness.

Generating longitudinal non-conforming data records, also referred to as composite medical records, may make processing of medical data more efficient. For example, if all the medical data corresponding to a patient for a day were stored in a single record, a system may be able to query for that single record and provide the single record instead of generating multiple queries to multiple separate different databases and join together multiple records provided in response by the multiple separate different databases. Additionally, the single records may be distributed between multiple databases enabling efficiency provided by parallel computing. Longitudinal non-conforming data records that are sorted for time series analysis, and partitioned and ordered across many machines, may enable patient studies across the entire population (e.g., no sampling) by doing various data analysis operations in memory, in parallel and iteratively (e.g., projections, longitudinal metrics, stability and eligibility, bucketing, etc.), avoiding disk I/O and gaining tremendous efficiencies in processing time.

In one aspect, some implementations provide a computer-implemented method that includes actions of obtaining healthcare records from multiple different data sources that each provide information regarding a corresponding type of healthcare events, identifying healthcare records from the multiple different data sources that are for a healthcare event associated with a particular individual and that occurred during a particular period of time, and generating a composite record for the particular individual for the particular period of time. The composite record includes an identifier for the particular individual, a pharmaceutical transactions array, where each entry in the pharmaceutical transactions array represents a pharmaceutical transaction that occurred during the particular period of time, and a medical visit array, where each entry in the medical visit array represents a medical visit that occurred during the particular period of time. Further actions include storing the composite record in a database of composite records.

Implementations may include one or more of the following features. In certain aspects actions include storing a second composite record for the particular individual for a second particular period of time. In some aspects the particular period of time is a particular day. In some implementations each of the entries in the medical visit array include a medical procedure array that includes zero or more entries, where each entry in the medical procedure array represents a medical procedure that occurred during the corresponding medical visit. In certain aspects obtaining healthcare records from multiple different data sources that each provide information regarding a corresponding type of healthcare events includes obtaining pharmaceutical transaction information from a pharmaceutical transaction database where each record in the pharmaceutical transaction database represents a pharmaceutical transaction and obtaining medical visit information from a database from a medical visit database where each record in the medical visit database represents a medical visit.

In some aspects identifying healthcare records from the multiple different data sources that are for a healthcare event associated with a particular individual and that occurred during a particular period of time includes determining that the pharmaceutical transaction information indicates that a pharmaceutical transaction occurred for the particular user during the particular period of time and determining that the medical visit information indicates that a medical visit occurred for the particular user during the particular period of time. In some implementations the pharmaceutical transactions array in the composite record for the particular individual for the particular period of time includes an entry for each of the pharmaceutical transaction indicated by the healthcare records. In certain aspects the medical visit array in the composite record for the particular individual for the particular period of time includes an entry for each of the medical visits indicated by the healthcare records. In some aspects the entries in the pharmaceutical transactions array are sorted by a time when the pharmaceutical transaction represented by the entry occurred.

In certain aspects actions include receiving a request for healthcare information regarding patients that obtained a pharmaceutical at a particular time, determining that the particular time occurred during the particular period of time, in response to determining that the particular time occurred during the particular period of time, obtaining the composite record for the particular individual for the particular period of time, determining whether the pharmaceutical transactions array includes an entry for the pharmaceutical at the particular time, and in response to determining that the pharmaceutical transactions array includes an entry for the pharmaceutical at the particular time, providing information about the particular individual in response to the request. In some aspects actions include receiving a request for healthcare information regarding patients that obtained a pharmaceutical at a particular time, determining that the particular time occurred during the particular period of time, in response to determining that the particular time occurred during the particular period of time, obtaining the composite record for the particular individual for the particular period of time, determining whether the pharmaceutical transactions array includes an entry for the pharmaceutical at the particular time, and in response to determining that the pharmaceutical transactions array does not include an entry for the pharmaceutical at the particular time, determining not to provide information about the particular individual for the particular time period in response to the request.

The details of one or more aspects of the subject matter described in this specification are set forth in the accompanying drawings and the description below. Other features, aspects, and advantages of the subject matter will become apparent from the description, the drawings, and the claims.

DESCRIPTION OF DRAWINGS

Like reference symbols in the various drawings indicate like elements.

DETAILED DESCRIPTION

Figure 1:
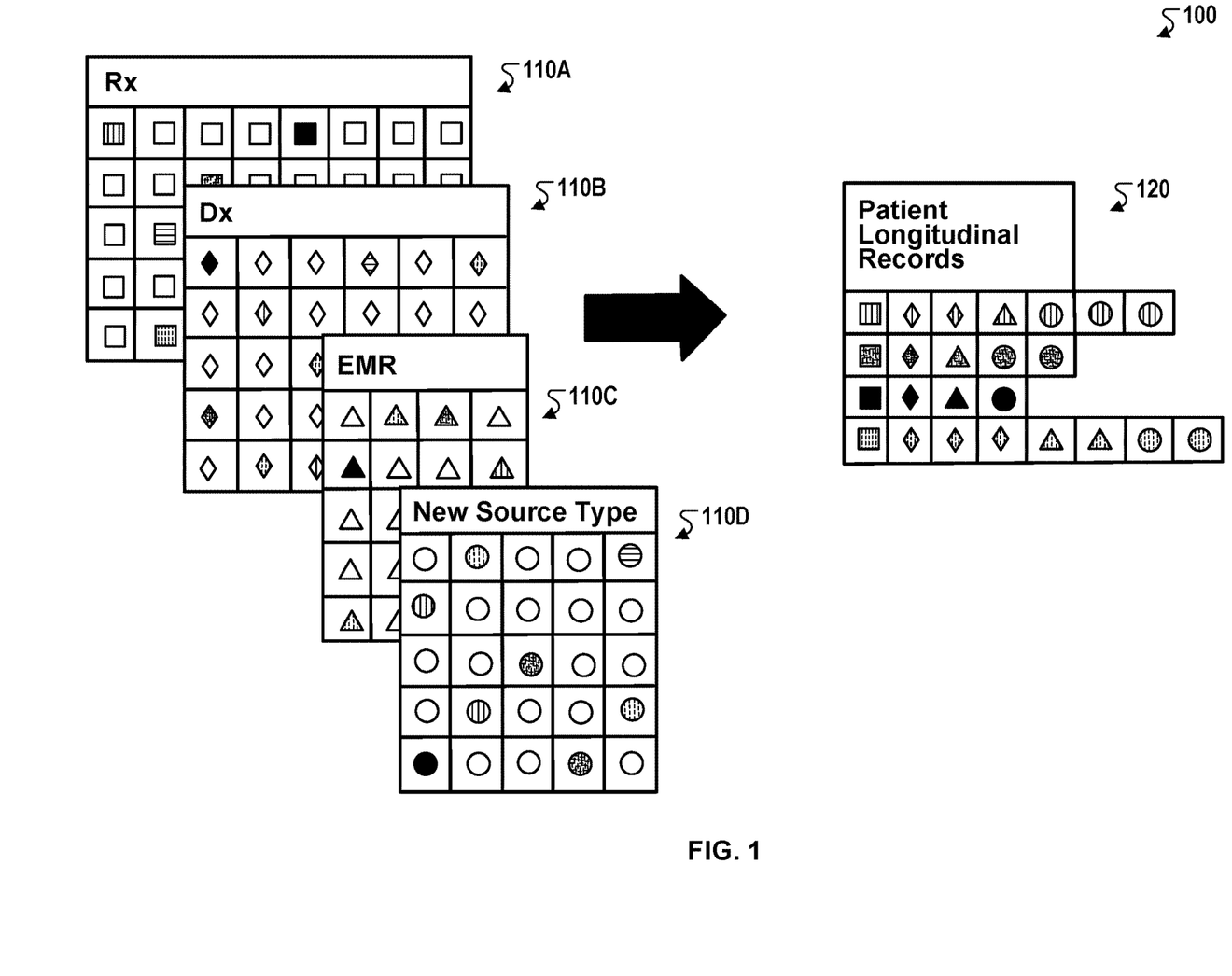
FIGS. 1 and 2 illustrate examples of a system for generating longitudinal non-conforming medical data records.

FIG. 1 illustrates an example of a system 100 for generating longitudinal non-conforming medical records. The system 100 may obtain medical data records from multiple different data sources and generate longitudinal non-conforming medical records from the obtained medical data records. For example, the system 100 may obtain prescription records from a prescription data source 110A, doctor visit records from a doctor visit data source 110B, medical procedure records from an emergency medical record data source 110C, and any other new type of record from a new source type data source 110D. The prescription records may include prescriptions by time. For example, a first row of prescription records may indicate that during a first time period, prescriptions for a first patient and a second patient were received. A second row of prescription records may indicate that during a second time period, only a prescription for a third patient was received. Each shape in the records shown in FIG. 1 may correspond to a particular type of data, shaded shapes may correspond to data of interest, and each type of shading pattern may correspond to a different de-identified patient.

In the system, records may generally be for different anonymized patients, where each record identifies one or more medical events and an identifier that uniquely distinguishes the anonymized patient from other anonymized patients. The identifier may refer to a de-identified patient, which may also be referred to as an anonymized patient. The de-identification means no identity information, such as name, address, birth date, or social security information, is available in the recorded information. Instead, each patient is referenced by an anonymous tag that is specific to the patient. Accordingly, an anonymized patient may be a patient for which the patient's identity cannot be determined but is distinguishable from other anonymized patients. Generally, the anonymous tag is doubly encrypted using a key specific to a data supplier (such as a data server at a pharmacy) and another key specific to a longitudinal database.

Data corresponding to the same participant patient may be linked by virtue of the matching the anonymous tag. Thus, data for the same participant patient may be longitudinally tracked for each individual, without compromising confidentiality of the individual patients, even though the patient can fill the prescription at various stores and the patient can receive a prescription for a healthcare product from various healthcare professionals.

The longitudinal non-conforming medical records may aggregate information from the various data sources 110 (collectively referring to data sources 110A, 110B, 110C, and 110D) together and generate a record for each patient for a period of time. For example, a first row in the longitudinal non-conforming medical records may include information that indicates all prescriptions, medical visits, and medical procedures that occurred for a particular patient during a particular day, a second row in the longitudinal non-conforming medical records may include information that indicates all prescriptions, medical visits, and medical procedures that occurred for another patient during a particular day, and a third row in the longitudinal non-conforming medical records may include information that indicates all prescriptions, medical visits, and medical procedures that occurred for the particular patient during another day. A medical event may refer to an event of interest that is indicated by records. For example, a medical event may be a prescription being fulfilled, a doctor visit, or a procedure being performed. As the number of medical events per day for a patient may vary, a longitudinal non-conforming medical record may be unbounded in regard to the number of medical events for which the record may include information. For example, the first row in the longitudinal non-conforming medical records includes seven events and the second row includes five entries.

Figure 2:
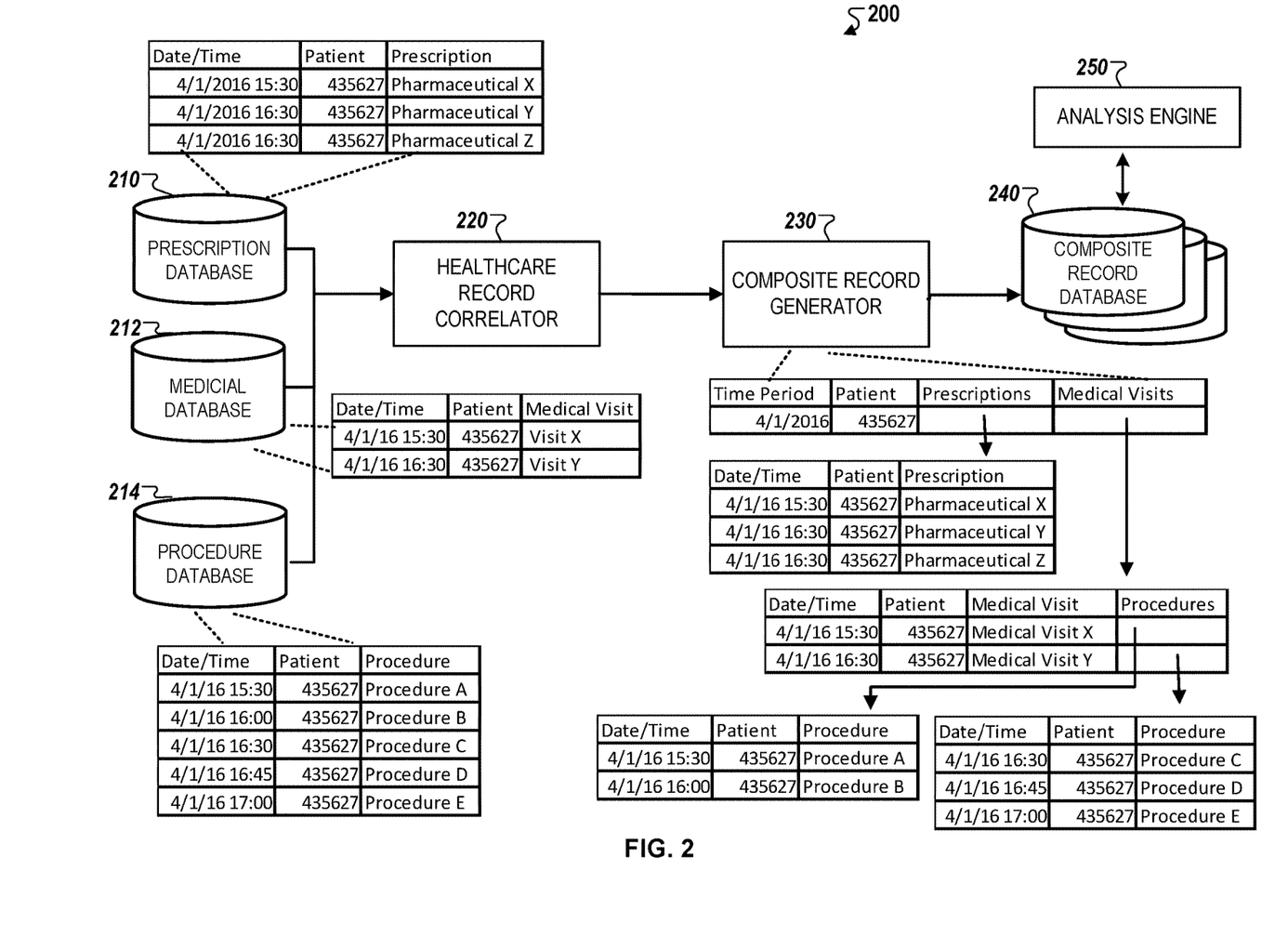

FIG. 2 illustrates an example of a system 200 for generating longitudinal non-conforming medical data records. The system 200 may include a prescription database 210 that includes prescription records, a medical database 212 that includes medical visit records, a procedure database 214 that includes medical procedure records, a healthcare record correlator 220 that identifies relationships between the prescription records, medical visit records, and the medical procedure records, a composite record generator 230 that generates composite records from the correlated records, a composite record database 240 that stores the composite records, and an analysis engine 250 that analyzes the composite data records.

In more detail, the prescription database 210 may include multiple records where each record may represent a prescription that was fulfilled. For example, a first record may represent a prescription for "Pharmaceutical X" that was fulfilled for a patient with the de-identified tag "435627" at Apr. 1, 2016 3:30 PM, a second record may represent a prescription for "Pharmaceutical Y" that was fulfilled for the same patient with the de-identified tag "435627" at Apr. 1, 2016 4:30 PM, and a third record may represent a prescription for "Pharmaceutical Z" that was fulfilled for the same patient with the de-identified tag "435627" at Apr. 1, 2016 4:30 PM. While in FIG. 2 all the prescription records shown are for the patient with the de-identified tag "435627" on Apr. 1, 2016, the prescription database 210 may include additional records for other patients and other times of fulfillment. Additionally or alternatively, each of the prescription records may include other information. For example, each record may include an insurance claim identifier, field of price, health insurance, pharmacy location, and other prescription related information.

The medical visit database may include multiple records where each record may represent a medical visit. For example, a first record may represent "Medical Visit X" made by a patient with the de-identified tag "435627" at Apr. 1, 2016 3:30 PM and a second record may represent "Medical Visit Y" made by the same patient with the de-identified tag "435627" at Apr. 1, 2016 4:30 PM. While in FIG. 2 all the medical visit records shown are for the patient with the de-identified tag "435627" on Apr. 1, 2016, the medical database 212 may include additional records for other patients and other times of medical visits. Additionally or alternatively, each of the medical visit records may include other information. For example, each record may include fields for an insurance claim identifier, a diagnosis, a place of service, health insurance, and other medical visit related information.

The procedure database 214 may include multiple records where each record may represent a medical procedure. For example, a first record may represent "Procedure A" made for a patient with the de-identified tag "435627" at Apr. 1, 2016 3:30 PM, a second record may represent "Procedure B" made by the same patient with the de-identified tag "435627" at Apr. 1, 2016 4:00 PM, a third record may represent "Procedure C" made for a patient with the de-identified tag "435627" at Apr. 1, 2016 4:30 PM, a fourth record may represent "Procedure D" made by the same patient with the de-identified tag "435627" at Apr. 1, 2016 4:45 PM, and a fifth record may represent "Procedure E" made by the same patient with the de-identified tag "435627" at Apr. 1, 2016 5:00 PM. While in FIG. 2 all the procedure records shown are for the patient with the de-identified tag "435627" on Apr. 1, 2016, the procedure database 214 may include additional records for other patients and other times of medical visits. Additionally or alternatively, each of the procedure records may include other information. For example, each record may include fields for an insurance claim identifier, a place of service, an identifier for a medical visit record representing a medical visit during which the procedure occurred, and other medical visit related information.

The healthcare record correlator 220 may identify relationships between the prescription records, the medical visit records, and the medical procedure records. For example, the healthcare record correlator 220 may determine that a set of prescription records, medical visit records, and medical procedure records all include a patient value of the de-identified tag "435627." In some implementations, the healthcare record correlator 220 may generate or map de-identified tags between the various types of records. For example, the healthcare record correlator 220 may determine that a patient de-identified tag of "435627" for a prescription record corresponds to a patient de-identified tag of "851532" for a medical procedure record so that the prescription and medical procedure were for the same unidentifiable person.

The healthcare record correlator 220 may determine which medical procedures occurred during which medical visits. For example, the healthcare record correlator 220 may determine that "Procedure B" occurred during "Visit X" because "Procedure B" occurred at or after "Visit X" started and before "Visit Y" started. In another example, the healthcare record correlator 220 may determine that "Procedure D" occurred during "Visit Y" because the medical visit that most recently occurred at or before "Procedure D" occurred is "Visit Y." Accordingly, for each medical procedure, the healthcare correlator 220 may identify the medical visit that occurred at or most recently before the medical procedure and associate the medical procedure as occurring during that medical visit. Alternatively where the medical procedure records include a field indicating a medical visit identifier, the healthcare record correlator 220 may identify a medical visit record that corresponds to that medical visit identifier and associate the medical procedures with those matching medical visits.

The composite record generator 230 may generate composite records that each represent all the medical events for a de-identified patient for a particular period of time. For example, the composite record generator 230 may generate a single composite record for all prescriptions fulfilled for, medical visits occurring for, or medical procedures performed for de-identified patient "435627" on Apr. 1, 2016. Accordingly, when medical events for a de-identified patient for a particular period of time are to be analyzed, the single composite record can be obtained instead of multiple records from multiple different data sources that then may need to be transformed and joined together. While the particular period of time shown in FIG. 2 is one day, the particular period of time may be instead be one hour, twelve hours, a week, or some other period of time. In some implementations, the particular period of time may be specified by an administrator of the system 200.

Each of the composite records may include predetermined fields but be non-conforming and unbounded. For example, each composite records may include a field that indicates a time period, a field that indicates a de-identified patient, a field that indicates an array of prescriptions, and a field that indicates an array of medical visits. The composite records may be considered to be unbounded and non-conforming as, although each record includes the same fields, the number of medical events indicated by the composite record may differ. For example, a first composite record may have an array of prescriptions that includes two entries for two different prescriptions that were fulfilled and a second composite record may have an array of prescriptions that includes three entries for three different prescriptions that were fulfilled.

The array of prescriptions may include entries for each of the prescriptions indicated by the prescription records for that time period. For example, the array of prescriptions may include three entries for the three prescriptions for a particular day for a patient with de-identified tag of "435627" indicated by the prescription records. The array of medical visits may include entries for each of the medical visits indicated by the medical visit records for that time period. For example, the array of medical visits may include two entries for the two medical visits for a particular day for a patient with de-identified tag of "435627" indicated by the medical visit records. Each of the entries in the array of medical visits may also indicate an array of medical procedures indicated by the procedure records. For example, the entry for "Medical Visit X" may indicate an array of medical procedures that includes two entries and the entry for "Medical Visit Y" may indicate an array of medical procedures that include three entries. Each of the entries in the medical procedure array may also include a field indicating a diagnosis. For example, the procedure records may indicate that "Procedure A" was associated with "Diagnosis X," "Procedure B" was associated with "Diagnosis X," "Procedure C" was associated with "Diagnosis X," "Procedure D" was associated with "Diagnosis Y," and "Procedure E" was associated with "Diagnosis Y," and the entries for the procedures in the array of medical procedures may similarly indicate the diagnosis that led to each procedure. In some implementations, the entries in the arrays may be ordered by time to increase efficiency in locating an entry.

Accordingly, each of the composite records may represent all known medical events that occurred during a time period for a de-identified patient and eliminate the need for joining multiple records in providing information on medical events that occurred for a de-identified patient and during a time period.

The composite record generator 230 may generate composite records based on receiving a set of correlated records from the healthcare record correlator 220. For example, the composite record generator 230 may receive a set of records from the healthcare record correlator 220 that are all for a particular de-identified patient and process the records in the set of records. Additionally or alternatively, the composite record generator 230 may iteratively proceed through each record in the prescription database 210, the medical database 212, and the procedure database 214.

Where a composite record does not exist for the de-identified patient for a particular time period during which a prescription record indicates that a prescription was fulfilled, the composite record generator 230 may generate a new composite record for the de-identified patient for the particular time period. For example, the composite record generator 230 may obtain a prescription record that is for Apr. 1, 2016, 3:30 PM for patient "435627" and determine that Apr. 1, 2016, 3:30 PM corresponds to a particular day time period Apr. 1, 2016 and that no composite record exists for patient "435627" for Apr. 1, 2016. In response, the composite record generator 230 may generate a composite record with a time period of Apr. 1, 2016, with a de-identified patient tag of "435627," with a prescription array that just includes an entry for the prescription with prescription information from the prescription record, and with a medical visit array that includes no entries.

Where a composite record does exist for the de-identified patient for a particular time period during which a prescription record indicates that a prescription was fulfilled, the composite record generator 230 may add an entry for the prescription into the prescription array in the composite record. For example, the composite record generator 230 may obtain a prescription record that is for Apr. 1, 2016, 4:30 PM for patient "435627" and determine that Apr. 1, 2016, 4:30 PM corresponds to a day time period Apr. 1, 2016 and that a composite record exists for patient "435627" for Apr. 1, 2016. In response, the composite record generator 230 may add an entry into the prescription array including information from the prescription record so that the entry is in a position so that the entries in the prescription array are ordered by ascending time. The composite record generator 230 may similarly process the medical records from the medical database 212 and the procedure records from the procedure record database 214.

The composite record generator 230 may store the composite records among multiple servers of the composite record database 240. For example, the composite record generator 230 may store composite records for March for all patients on a first server of the database 240 and composite records for April for all patients on a second server of the database 240. Accordingly, the system 200 may process the composite records in parallel, resulting in greater efficiency.

The analysis engine 250 may perform analysis on the composite record database 240. For example, the analysis engine 250 may identify a de-identified tag for all patients that received a particular type of medical procedure on Apr. 1, 2016. In another example, the analysis engine 250 may provide a history of all medical events that occurred for a particular de-identified patient during a particular time period. In still another example, the analysis engine 250 may provide a longitudinal history of all medical events that occurred for a particular de-identified patient across a time period covered by multiple composite records, e.g., a two year period where each composite record covers one week and the longitudinal history is obtaining from the corresponding one hundred and four composite records for the corresponding weeks in the two year period.

The analysis engine 250 may perform analysis efficiently as the analysis engine 250 may leverage the fact that all medical events for each de-identified patient that occurred during a particular time period should be in a single composite record for the de-identified patient, and the prescriptions, medical visits, and medical procedures are already respectively sorted by time. For example, if the analysis engine 250 determines that a composite record for a particular de-identified patient for a particular time period does not exist, then the analysis engine 250 may determine that no medical events occurred for the de-identified patient for the particular time period. Similarly, the analysis engine 250 may determine that if a prescription array, medical visit array, or medical procedure array does not include an entry that matches criteria in a request, then no information for a prescription, a medical visit, or a medical procedure matches the criteria in the request. Accordingly, the analysis engine 250 may not need to query multiple different types of databases.

In another example, if the analysis engine 250 is providing all medical events that occurred during a particular time period for de-identified patients that satisfy a criteria, once the analysis engine 250 determines a de-identified patient satisfies the criteria based on information in the composite record for the de-identified patient for the particular time period, the analysis engine 250 may provide just information in the composite record as the composite record already includes information for all medical events that occurred during the particular time period for the de-identified patient. Accordingly, the analysis engine 250 may avoid needing to provide a separate subsequent query for additional information on medical events for de-identified patients that satisfy a criteria.

In a more detailed example, if the analysis engine 250 receives a request for a de-identified tag for all de-identified patients that received a particular type of medical procedure on Apr. 1, 2016 between 2 PM-4 PM, the analysis engine 250 may identify all composite records for Apr. 1, 2016, for each of the identified records, identify all medical visit entries for medical visits that occurred at or before 4 PM, and for each identified medical visit entry, determine whether a medical procedure entry exists for the medical visit entry indicating a medical procedure of the particular type occurred between 2 PM-4 PM, and if so, providing the de-identified tag in the composite record, and if not, not provide the de-identified tag in the composite record. Accordingly, the analysis engine may avoid needing to provide a separate subsequent query for additional information on medical events for de-identified patients that satisfy a criteria.

Additionally, the analysis engine 250 may perform analysis efficiently as the analysis engine 250 may leverage that the composite records are distributed between multiple servers of the composite record database 240 that may provide results in parallel. For example, when the analysis engine 250 receives a request to identify all patients that were prescribed "Pharmaceutical X" during March or April, the system 200 may provide a first request to a first server of the database that stores composite records for March and a second request to a second server of the database that stores composite records for April, to identify patients in parallel. Other requests that leverage the composite records may include "Find me all de-identified patients over the past 2 years who have taken a particular drug, in New Jersey, between the age to 10 and 85 and are Male," "Find me all the prescriptions, procedures, and diagnoses of a de-identified patient has taken over the past 8 months, organized by time," "Find me all the de-identified patients over the past 3 years who have had Procedure A and taken prescriptions A or B," and "Find me all the de-identified patients over the past 3 years who have had Procedure A and taken prescriptions A and switched to prescription B."

Different configurations of the system 200 may be used where functionality of the prescription database 210, the medical database 212, the procedure database 214, the healthcare record correlator 220, the composite record generator 230, the composite record database 240, and the analysis engine 250 may be combined, further separated, distributed, or interchanged. For example, the composite record generator 230 may perform the functions of the healthcare record correlator 220. In another example, the healthcare record correlator 220 may obtain the prescription records, medical records, and procedure records from a single database that includes different respective data structures for each type of record instead of obtaining the records from separate databases.

Figure 3:
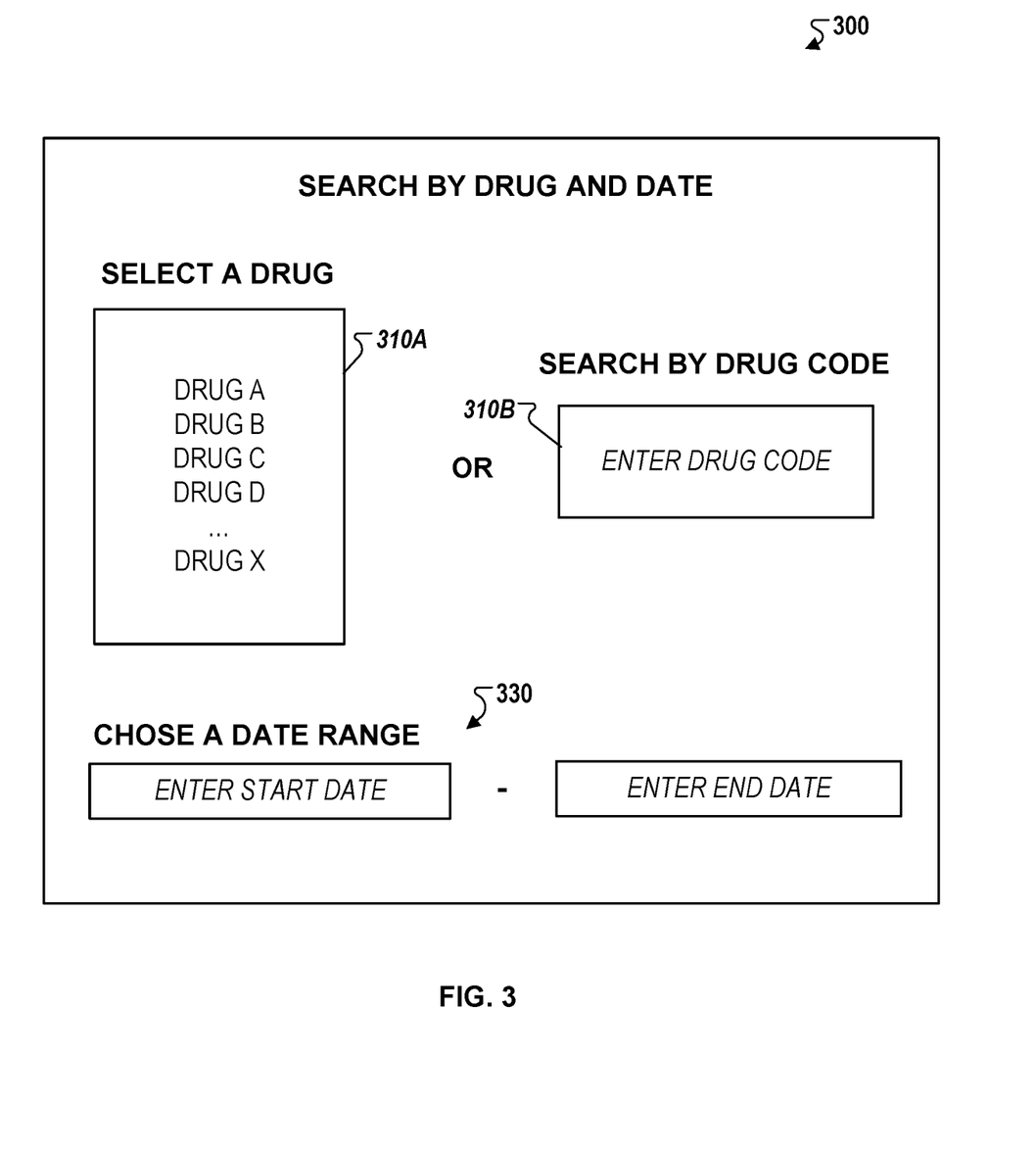
FIG. 3 illustrates a graphical user interface for searching in a system using longitudinal non-conforming medical data records.

FIG. 3 illustrates a graphical user interface 300 for searching in a system using longitudinal non-conforming medical data records. The interface 300 includes control elements 310A, 310B for specifying a drug and control elements 330 for specifying a start date and end date for a search request for medical events of de-identified patients that took the specified drug during the date range beginning at the specified start date and ending at the end date. For example, a user may select "Drug B" and enter a start date of Mar. 1, 2016 and an end date of Apr. 30, 2016 to request information on de-identified patients that had a prescription fulfilled for "Drug B" on or between Mar. 1, 2016 and Apr. 30, 2016. Other graphical user interfaces may additionally or alternatively be used. For example, the different example requests previously discussed may each be associated with a different corresponding interface.

Figure 4:
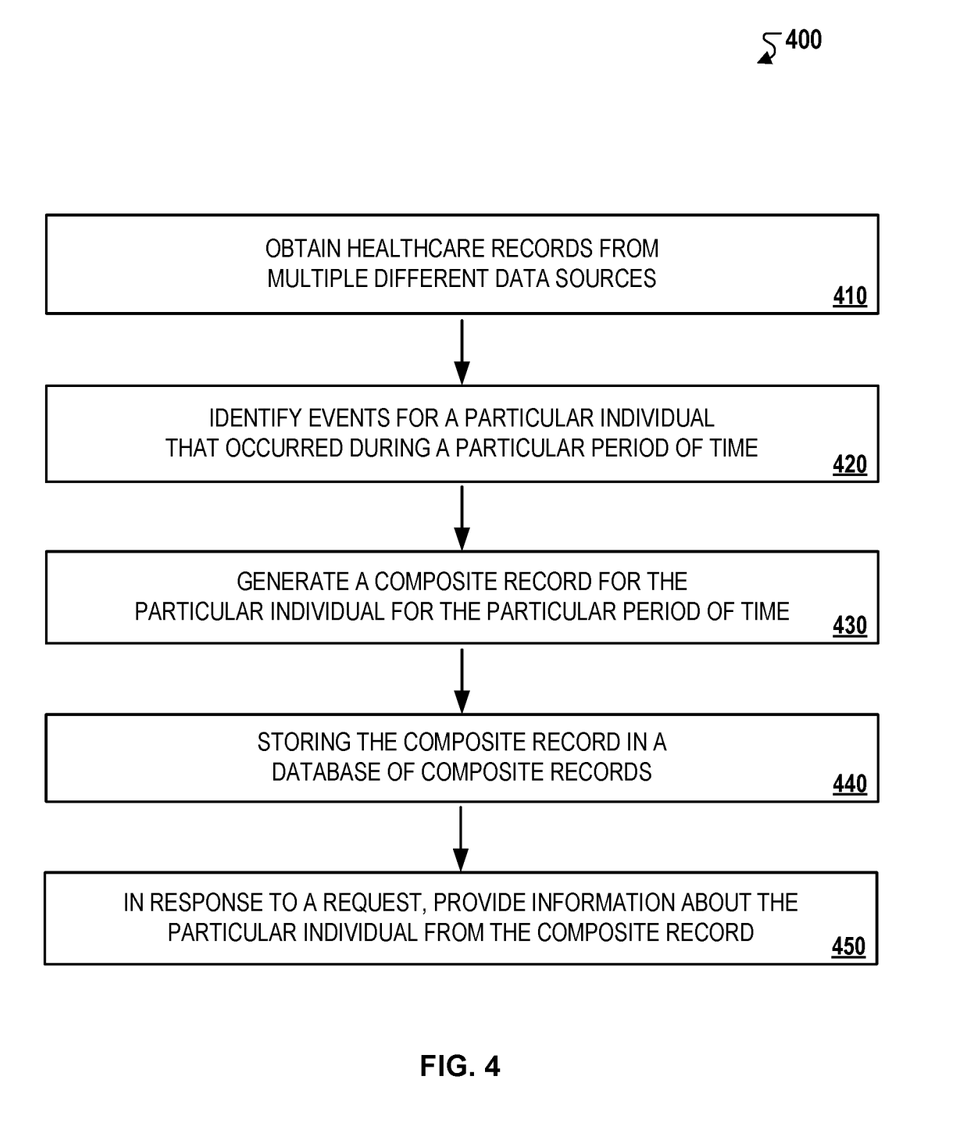
FIG. 4 illustrates an example of a flow chart for generating longitudinal non-conforming medical data records.

FIG. 4 illustrates an example flowchart of a process 400 for generating longitudinal non-conforming medical data records. Initially, healthcare records from multiple different data sources are obtained (410). For example, the healthcare record correlator 220 may obtain prescription records from the prescription database 210, medical visit records from the medical database 212, and procedure records from the procedure database 214. In some implementations, other data sources may be used. For example, only a prescription database and medical database may be used, or an additional different type of database may be used.

Events for a particular individual that occurred during a particular period of time may be identified (420). For example, the healthcare record correlator 220 may cluster the various records into sets where each set includes all records for a de-identified patient for a particular day.

A composite record for the particular individual for the particular period of time may be generated (430). For example, the composite record generator 230 may generate a composite record for a patient with a de-identified tag of "657483" for Apr. 1, 2016, where the composite record includes an identifier for the particular individual, a pharmaceutical transactions array, where each entry in the pharmaceutical transactions array represents a pharmaceutical transaction that occurred during the particular period of time, and a medical visit array, where each entry in the medical visit array represents a medical visit that occurred during the particular period of time, where the medical visit array can include zero to many entries for medical visits for a single time period. Each of the entries in the medical visit array may include a medical procedure array, where each entry in the medical procedure array represents a medical procedure that occurred during the particular medical visit, where the medical procedure array can include zero to many entries for medical procedures for a single medical visit.

The composite record may be stored in a database of composite records (440). For example, the composite record generator 230 may store the composite record for a patient with a de-identified tag of "657483" for Apr. 1, 2016 in a particular database of composite records that stores composite records for all patients for all records for April. In another example, the composite record generator 230 may store the composite record for a patient with a de-identified tag of "657483" for Apr. 1, 2016 in a particular database of composite records that stores composite records for all patients for all records for March and April. The above actions may be repeated for other particular time periods and for other de-identified patients.

Information about the particular individual from the composite record may be provided in response to a request (450). For example, the analysis engine 250 may obtain a request for all medical events that occurred for any de-identified patient that fulfilled a prescription for a "Drug B" on Apr. 1, 2016, the analysis engine 250 may determine that the patient associated with the de-identified tag "657483" fulfilled a prescription for "Drug B" on Apr. 1, 2016 based on identifying an entry in the prescription array in the composite record for Apr. 1, 2016 for the patient indicating that a prescription for "Drug B" was fulfilled, and in response, provide the composite record.

Figure 5:
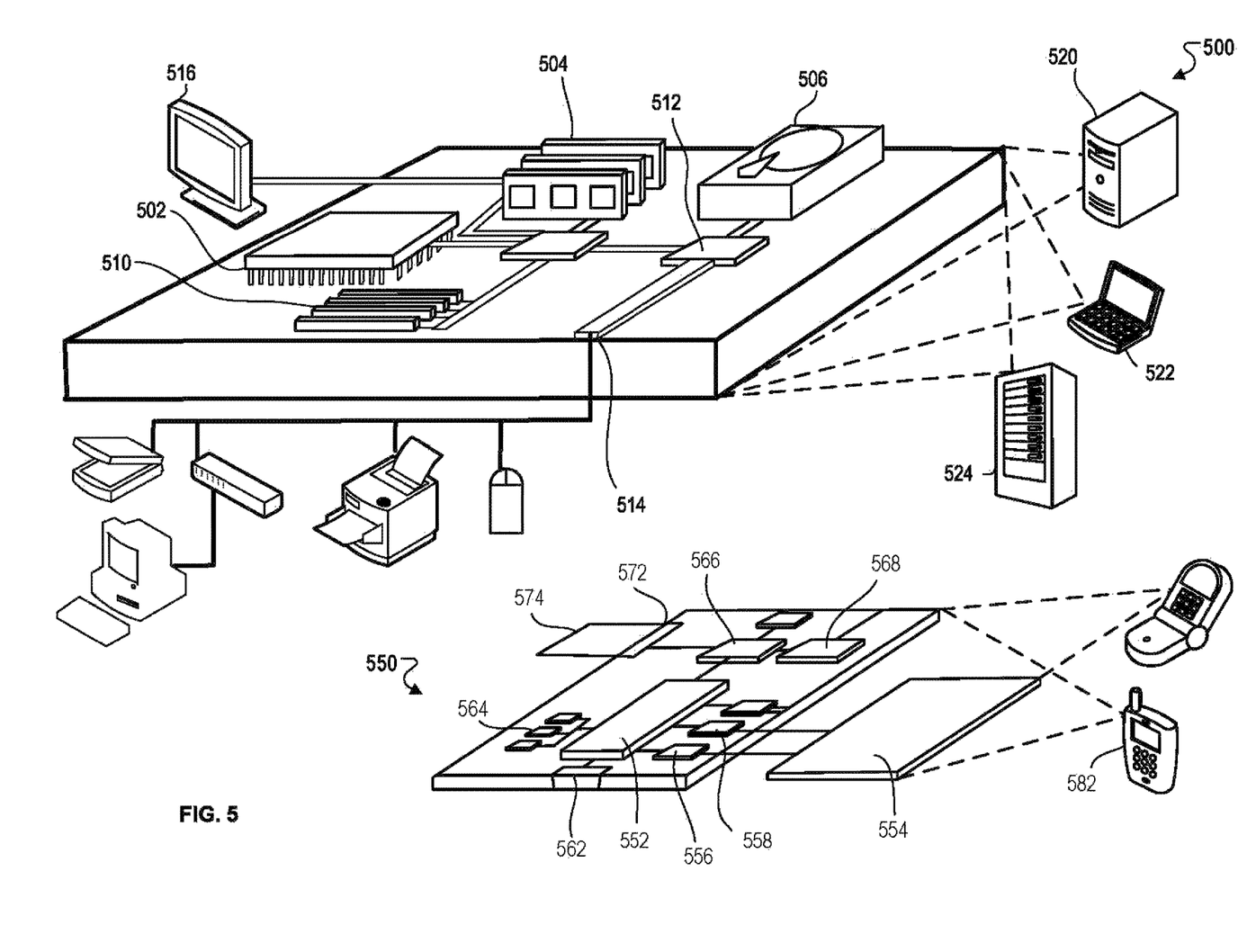
FIG. 5 is a block diagram of computing devices on which the processes described herein, or potions thereof, may be implemented.

FIG. 5 shows an example of a computing device 500 and a mobile computing device 550 that can be used to implement the techniques described here. The computing device 500 is intended to represent various forms of digital computers, such as laptops, desktops, workstations, personal digital assistants, servers, blade servers, mainframes, and other appropriate computers. The mobile computing device 550 is intended to represent various forms of mobile devices, such as personal digital assistants, cellular telephones, smart-phones, and other similar computing devices. The components shown here, their connections and relationships, and their functions, are meant to be examples only, and are not meant to be limiting.

The computing device 500 includes a processor 502, a memory 504, a storage device 506, a high-speed interface 508 connecting to the memory 504 and multiple high-speed expansion ports 510, and a low-speed interface 512 connecting to a low-speed expansion port 514 and the storage device 506. Each of the processor 502, the memory 504, the storage device 506, the high-speed interface 508, the high-speed expansion ports 510, and the low-speed interface 512, are interconnected using various busses, and may be mounted on a common motherboard or in other manners as appropriate. The processor 502 can process instructions for execution within the computing device 500, including instructions stored in the memory 504 or on the storage device 506 to display graphical information for a graphical user interface (GUI) on an external input/output device, such as a display 516 coupled to the high-speed interface 508. In other implementations, multiple processors and/or multiple buses may be used, as appropriate, along with multiple memories and types of memory. Also, multiple computing devices may be connected, with each device providing portions of the necessary operations (e.g., as a server bank, a group of blade servers, or a multi-processor system).

The memory 504 stores information within the computing device 500. In some implementations, the memory 504 is a volatile memory unit or units. In some implementations, the memory 504 is a non-volatile memory unit or units. The memory 504 may also be another form of computer-readable medium, such as a magnetic or optical disk.

The storage device 506 is capable of providing mass storage for the computing device 500. In some implementations, the storage device 506 may be or contain a computer-readable medium, such as a floppy disk device, a hard disk device, an optical disk device, or a tape device, a flash memory or other similar solid state memory device, or an array of devices, including devices in a storage area network or other configurations. Instructions can be stored in an information carrier. The instructions, when executed by one or more processing devices (for example, processor 502), perform one or more methods, such as those described above. The instructions can also be stored by one or more storage devices such as computer- or machine-readable mediums (for example, the memory 504, the storage device 506, or memory on the processor 502).

The high-speed interface 508 manages bandwidth-intensive operations for the computing device 500, while the low-speed interface 512 manages lower bandwidth-intensive operations. Such allocation of functions is an example only. In some implementations, the high-speed interface 508 is coupled to the memory 504, the display 516 (e.g., through a graphics processor or accelerator), and to the high-speed expansion ports 510, which may accept various expansion cards (not shown). In the implementation, the low-speed interface 512 is coupled to the storage device 506 and the low-speed expansion port 514. The low-speed expansion port 514, which may include various communication ports (e.g., USB, Bluetooth, Ethernet, wireless Ethernet) may be coupled to one or more input/output devices, such as a keyboard, a pointing device, a scanner, or a networking device such as a switch or router, e.g., through a network adapter.

The computing device 500 may be implemented in a number of different forms, as shown in the figure. For example, it may be implemented as a standard server 520, or multiple times in a group of such servers. In addition, it may be implemented in a personal computer such as a laptop computer 522. It may also be implemented as part of a rack server system 524. Alternatively, components from the computing device 500 may be combined with other components in a mobile device (not shown), such as a mobile computing device 550. Each of such devices may contain one or more of the computing device 500 and the mobile computing device 550, and an entire system may be made up of multiple computing devices communicating with each other.

The mobile computing device 550 includes a processor 552, a memory 564, an input/output device such as a display 554, a communication interface 566, and a transceiver 568, among other components. The mobile computing device 550 may also be provided with a storage device, such as a micro-drive or other device, to provide additional storage. Each of the processor 552, the memory 564, the display 554, the communication interface 566, and the transceiver 568, are interconnected using various buses, and several of the components may be mounted on a common motherboard or in other manners as appropriate.

The processor 552 can execute instructions within the mobile computing device 550, including instructions stored in the memory 564. The processor 552 may be implemented as a chipset of chips that include separate and multiple analog and digital processors. The processor 552 may provide, for example, for coordination of the other components of the mobile computing device 550, such as control of user interfaces, applications run by the mobile computing device 550, and wireless communication by the mobile computing device 550.

The processor 552 may communicate with a user through a control interface 558 and a display interface 556 coupled to the display 554. The display 554 may be, for example, a TFT (Thin-Film-Transistor Liquid Crystal Display) display or an OLED (Organic Light Emitting Diode) display, or other appropriate display technology. The display interface 556 may comprise appropriate circuitry for driving the display 554 to present graphical and other information to a user. The control interface 558 may receive commands from a user and convert them for submission to the processor 552. In addition, an external interface 562 may provide communication with the processor 552, so as to enable near area communication of the mobile computing device 550 with other devices. The external interface 562 may provide, for example, for wired communication in some implementations, or for wireless communication in other implementations, and multiple interfaces may also be used.

The memory 564 stores information within the mobile computing device 550. The memory 564 can be implemented as one or more of a computer-readable medium or media, a volatile memory unit or units, or a non-volatile memory unit or units. An expansion memory 574 may also be provided and connected to the mobile computing device 550 through an expansion interface 572, which may include, for example, a SIMM (Single In Line Memory Module) card interface. The expansion memory 574 may provide extra storage space for the mobile computing device 550, or may also store applications or other information for the mobile computing device 550. Specifically, the expansion memory 574 may include instructions to carry out or supplement the processes described above, and may include secure information also. Thus, for example, the expansion memory 574 may be provided as a security module for the mobile computing device 550, and may be programmed with instructions that permit secure use of the mobile computing device 550. In addition, secure applications may be provided via the SIMM cards, along with additional information, such as placing identifying information on the SIMM card in a non-hackable manner.

The memory may include, for example, flash memory and/or NVRAM memory (non-volatile random access memory), as discussed below. In some implementations, instructions are stored in an information carrier that the instructions, when executed by one or more processing devices (for example, processor 552), perform one or more methods, such as those described above. The instructions can also be stored by one or more storage devices, such as one or more computer- or machine-readable mediums (for example, the memory 564, the expansion memory 574, or memory on the processor 552). In some implementations, the instructions can be received in a propagated signal, for example, over the transceiver 568 or the external interface 562. Embodiments of the subject matter, the functional operations and the processes described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible nonvolatile program carrier for execution by, or to control the operation of, data processing apparatus. Alternatively or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "data processing apparatus" encompasses all kinds of apparatus, devices, and machines for processing data, including by way of example a programmable processor, a computer, or multiple processors or computers. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a standalone program or as a module, component, subroutine, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit). Computers suitable for the execution of a computer program include, by way of example, can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few.

Computer readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous. Other steps may be provided, or steps may be eliminated, from the described processes. Accordingly, other implementations are within the scope of the following claims.

The invention claimed is:

1. A computer-implemented method comprising:
obtaining, by one or more processors, healthcare records from multiple different databases, wherein each healthcare record provides information regarding a corresponding type of healthcare event;
analyzing, by the one or more processors, the obtained healthcare records to identify a healthcare event that: (i) is associated with an individual, and (ii) occurred during a first period of time;
identifying, by the one or more processors, a first anonymous tag in at least one of the identified healthcare records, where the first anonymous tag is specific to the individual to associate healthcare events to the individual without revealing information that identifies the individual;
determining, by the one or more processors, for the healthcare event, a mapping of information in each of the identified healthcare records based on the first anonymous tag, wherein the first anonymous tag corresponds to pharmaceutical transactions and the mapping of information maps the first anonymous tag to a second anonymous tag, the second anonymous tag corresponding to medical transactions, wherein the second anonymous tag is different from the first anonymous tag and is specific to the individual to associate healthcare events to the individual without revealing information that identifies the individual;
generating, by the one or more processors, correlated healthcare records that include the identified healthcare records using the mapping of information, wherein the correlated healthcare records comprise different respective data structures for each type of included identified healthcare record;
processing, by the one or more processors, information obtained from the different respective data structures for each type of healthcare record;
generating, by the one or more processors, a composite record for the individual, wherein the composite record: includes an unbound range of non-conforming data entries that store information obtained from the identified healthcare records,
includes a pharmaceutical transactions array that represents data aggregated from a first type of healthcare record, wherein the pharmaceutical transactions array includes a first unbounded range of non-conforming data entries, and the entries represent the pharmaceutical transactions that occurred during the first period of time, and
includes a medical visit array that represents data aggregated from a second type of healthcare record, wherein the medical visits array includes a second unbounded range of non-conforming data entries, and the entries represents the medical transactions corresponding to a medical visit that occurred during the first period of time, the second unbounded range having a different number of non-conforming data entries than the first unbounded range;
storing, by the one or more processors, the processed information in predetermined fields of the composite record for the first period of time;
distributing, by the one or more processors, the composite record to a server in a plurality of servers for storage, wherein each server is associated with a time period and stores composite records associated with individuals;
receiving, by the one or more processors, a first request that includes criteria of an event, the request seeking to identify one or more anonymous individuals for the event;
in response to receiving the request, determining, by the one or more processors, one or more servers from the plurality of servers that satisfy the criteria of the event from the first request;
transmitting, by the one or more processors, a second request to each determined server of the one or more servers to identify the one or more anonymous individuals;
receiving, by the one or more processors and from one or more of the determined servers of the one or more servers, one or more composite records for the one or more anonymous individuals that satisfy the criteria of the event; and
providing, by the one or more processors, a response to the first request, the response including the one or more received composite records for the one or more anonymous individuals.

2. The computer-implemented method of claim 1, comprising:
storing, by the one or more processors, a second composite record for the individual for a second period of time.

3. The computer-implemented method of claim 1, wherein the first period of time is a particular day.

4. The computer-implemented method of claim 1, wherein each of the entries in the medical visit array include a medical procedure array that includes zero or more entries, where each entry in the medical procedure array represents a medical procedure that occurred during the corresponding medical visit.

5. The computer-implemented method of claim 1, wherein obtaining healthcare records from multiple different data sources comprises:
obtaining, by the one or more processors, pharmaceutical transaction information from a pharmaceutical transaction database where each record in the pharmaceutical transaction database represents a pharmaceutical transaction; and obtaining, by the one or more processors, medical visit information from a medical visit database where each record in the medical visit database represents a medical visit.

6. The computer-implemented method of claim 5, wherein identifying healthcare records for the healthcare event comprises:

determining, by the one or more processors, that the pharmaceutical transaction information indicates that a pharmaceutical transaction occurred for the individual during the first period of time; and determining, by the one or more processors, that the medical visit information indicates that a medical visit occurred for the individual during the first period of time.

7. The computer-implemented method of claim 1, wherein the pharmaceutical transactions array in the composite record for the individual for the first period of time includes an entry for each of the pharmaceutical transactions indicated by a first subset of the correlated healthcare records.

8. The computer-implemented method of claim 1, wherein the medical visit array in the composite record for the individual for the first period of time includes an entry for each of the medical visits indicated by a second subset of the correlated healthcare records.

9. The computer-implemented method of claim 1, wherein the entries in the pharmaceutical transactions array are sorted by a time when the pharmaceutical transaction represented by the entry occurred.

10. The computer-implemented method of claim 1, comprising:

receiving, by the one or more processors, a request for healthcare information regarding patients that obtained a pharmaceutical at a particular time;

determining, by the one or more processors, that the particular time occurred during the first period of time;

based on a determination that the particular time occurred during the first period of time, obtaining, by the one or more processors, the composite record for the particular individual for the first period of time;

determining, by the one or more processors, whether the pharmaceutical transactions array includes an entry for the pharmaceutical at the particular time; and based on a determination that the pharmaceutical transactions array does not include an entry for the pharmaceutical at the particular time, determining, by the one or more processors, not to provide information about the individual for the particular time as a response to the request.

11. A system comprising:

one or more computers and one or more storage devices storing instructions that are operable, when executed by the one or more computers, to cause the one or more computers to perform operations comprising:

obtaining, by one or more processors, healthcare records from multiple different databases, wherein each healthcare record provides information regarding a corresponding type of healthcare event;

analyzing, by the one or more processors, the obtained healthcare records to identify a healthcare event that: (i) is associated with an individual, and (ii) occurred during a first period of time;

identifying, by the one or more processors, a first anonymous tag in at least one of the identified healthcare records, where the first anonymous tag is specific to the individual to associate healthcare events to the individual without revealing information that identifies the individual;

determining, by the one or more processors, for the healthcare event, a mapping of information in each of the identified healthcare records based on the first anonymous tag, wherein the first anonymous tag corresponds to pharmaceutical transactions and the mapping of information maps the first anonymous tag to a second anonymous tag, the second anonymous tag corresponding to medical transactions, wherein the second anonymous tag is different from the first anonymous tag and is specific to the individual to associate healthcare events to the individual without revealing information that identifies the individual;

generating, by the one or more processors, correlated healthcare records that include the identified healthcare records using the mapping of information, wherein the correlated healthcare records comprise different respective data structures for each type of included identified healthcare record;

processing, by the one or more processors, information obtained from the different respective data structures for each type of healthcare record;

generating, by the one or more processors, a composite record for the individual, wherein the composite record: includes an unbound range of non-conforming data entries that store information obtained from the identified healthcare records, includes a pharmaceutical transactions array that represents data aggregated from a first type of healthcare record, wherein the pharmaceutical transactions array includes a first unbounded range of non-conforming data entries, and the entries represent the pharmaceutical transactions that occurred during the first period of time, and includes a medical visit array that represents data aggregated from a second type of healthcare record, wherein the medical visits array includes a second unbounded range of non-conforming data entries, and the entries represents the medical transactions corresponding to a medical visit that occurred during the first period of time, the second unbounded range having a different number of non-conforming data entries than the first unbounded range;

storing, by the one or more processors, the processed information in predetermined fields of the composite record for the first period of time;

distributing, by the one or more processors, the composite record to a server in a plurality of servers for storage, wherein each server is associated with a time period and stores composite records associated with individuals;

receiving, by the one or more processors, a first request that includes criteria of an event, the request seeking to identify one or more anonymous individuals for the event;

in response to receiving the request, determining, by the one or more processors, one or more servers from the plurality of servers that satisfy the criteria of the event from the first request;

transmitting, by the one or more processors, a second request to each determined server of the one or more servers to identify the one or more anonymous individuals;

receiving, by the one or more processors and from one or more of the determined servers of the one or more servers, one or more composite records for the one or more anonymous individuals that satisfy the criteria of the event; and providing, by the one or more processors, a response to the first request, the response including the one or more received composite records.

12. The system of claim 11, comprising:

storing, by the one or more processors, a second composite record for the individual for a second period of time.

13. The system of claim 11, wherein the first period of time is a particular day.

14. The system of claim 11, wherein each of the entries in the medical visit array include a medical procedure array that includes zero or more entries, where each entry in the medical procedure array represents a medical procedure that occurred during the corresponding medical visit.

15. The system of claim 11, wherein obtaining healthcare records from multiple different data sources comprises:

obtaining, by the one or more processors, pharmaceutical transaction information from a pharmaceutical transaction database where each record in the pharmaceutical transaction database represents a pharmaceutical transaction; and obtaining, by the one or more processors, medical visit information from a medical visit database where each record in the medical visit database represents a medical visit.

16. The system of claim 15, wherein identifying healthcare records for the healthcare event comprises:

determining, by the one or more processors, that the pharmaceutical transaction information indicates that a pharmaceutical transaction occurred for the individual during the first period of time; and determining, by the one or more processors, that the medical visit information indicates that a medical visit occurred for the individual during the first period of time.

17. The system of claim 11, wherein the pharmaceutical transactions array in the composite record for the individual for the first period of time includes an entry for each of the pharmaceutical transactions indicated by a first subset of the correlated healthcare records.

18. The system of claim 11, wherein the medical visit array in the composite record for the individual for the first period of time includes an entry for each of the medical visits indicated by a second subset of the correlated healthcare records.

19. A non-transitory computer-readable medium storing software comprising instructions executable by one or more computers which, upon such execution, cause the one or more computers to perform operations comprising:

obtaining, by one or more processors, healthcare records from multiple different databases, wherein each healthcare record provides information regarding a corresponding type of healthcare event;

analyzing, by the one or more processors, the obtained healthcare records to identify a healthcare event that: (i) is associated with an individual, and (ii) occurred during a first period of time;

identifying, by the one or more processors, a first anonymous tag in at least one of the identified healthcare records, where the first anonymous tag is specific to the individual to associate healthcare events to the individual without revealing information that identifies the individual;

determining, by the one or more processors, for the healthcare event, a mapping of information in each of the identified healthcare records based on the first anonymous tag, wherein the first anonymous tag corresponds to pharmaceutical transactions and the mapping of information maps the first anonymous tag to a second anonymous tag, the second anonymous tag corresponding to medical transactions, wherein the second anonymous tag is different from the first anonymous tag and is specific to the individual to associate healthcare events to the individual without revealing information that identifies the individual;

generating, by the one or more processors, correlated healthcare records that include the identified healthcare records using the mapping of information, wherein the correlated healthcare records comprise different respective data structures for each type of included identified healthcare record;

processing, by the one or more processors, information obtained from the different respective data structures for each type of healthcare record;

generating, by the one or more processors, a composite record for the individual, wherein the composite record: includes an unbound range of non-conforming data entries that store information obtained from the identified healthcare records, includes a pharmaceutical transactions array that represents data aggregated from a first type of healthcare record, wherein the pharmaceutical transactions array includes a first unbounded range of non-conforming data entries, and the entries represent the pharmaceutical transactions that occurred during the first period of time, and includes a medical visit array that represents data aggregated from a second type of healthcare record, wherein the medical visits array includes a second unbounded range of non-conforming data entries, and the entries represents the medical transactions corresponding to a medical visit that occurred during the first period of time, the second unbounded range having a different number of non-conforming data entries than the first unbounded range;

storing, by the one or more processors, the processed information in predetermined fields of the composite record for the first period of time;

distributing, by the one or more processors, the composite record to a server in a plurality of servers for storage, wherein each server is associated with a time period and stores composite records associated with individuals;

receiving, by the one or more processors, a first request that includes criteria of an event, the request seeking to identify one or more anonymous individuals for the event;

in response to receiving the request, determining, by the one or more processors, one or more servers from the plurality of servers that satisfy the criteria of the event from the first request;

transmitting, by the one or more processors, a second request to each determined server of the one or more servers to identify the one or more anonymous individuals;

receiving, by the one or more processors and from one or more of the determined servers of the one or more servers, one or more composite records for the one or more anonymous individuals that satisfy the criteria of the event; and providing, by the one or more processors, a response to the first request, the response including the one or more received composite records.

20. The computer-implemented method of claim 1, wherein:

the composite record is configured to link data in the identified healthcare records for the same individual using the anonymous tag; and the linked data included in the composite record permits tracking of data related to healthcare events for the individual without compromising confidentiality of the individual.

21. The computer-implemented method of claim 1, wherein the composite record represents a single source of medical data for the individual and includes information describing a plurality of healthcare events that involve the individual, and wherein each healthcare event of the plurality of healthcare events occurred during the first period of time.

* * * * *